United States Patent [19]
van der Bruggen et al.

[11] Patent Number: 5,928,938
[45] Date of Patent: Jul. 27, 1999

[54] **ISOLATED PEPTIDES WHICH COMPLEX WITH HLA-CW*16 MOLECULES, AND USES THEREOF**

[75] Inventors: Pierre van der Bruggen; Etienne DePlaen; Thierry Boon-Falleur, all of Brussels, Belgium

[73] Assignee: Ludwig Institute for Cancer Research, New York, N.Y.

[21] Appl. No.: 08/993,738

[22] Filed: Dec. 19, 1997

Related U.S. Application Data

[62] Division of application No. 08/713,354, Sep. 13, 1996.

[51] Int. Cl.⁶ ............... C12N 15/63; C12N 15/85; C07H 21/04
[52] U.S. Cl. ............ 435/320.1; 435/325; 435/455; 536/23.5
[58] Field of Search ............... 435/320.1, 325, 435/455; 536/23.5

*Primary Examiner*—Thomas M. Cunningham
*Assistant Examiner*—Martha T. Lubet
*Attorney, Agent, or Firm*—Fulbright & Jaworski, LLP.

[57] ABSTRACT

The invention involves the identification of peptides which complex with HLA-Cw*16 molecules, and which may then provoke lysis of the cells to which they bind, by cytolytic T cells. Diagnostic and therapeutic uses are described.

3 Claims, 3 Drawing Sheets

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
      (A) LENGTH: 9 amino acid residues
      (B) TYPE: amino acid
      (D) TOPOLOGY: linear (xi) SEQUENCE DESCRIPTION: SEQ ID NO: 1:

Ala Ala Arg Ala Val Phe Leu Ala Leu
                5

(2) INFORMATION FOR SEQ ID NO: 2:

(i) SEQUENCE CHARACTERISTICS:
      (A) LENGTH: 1375 nucleotides (B) TYPE: nucleic acid
            (C) STRANDEDNESS: single
            (D) TOPOLOGY: linear (xi) SEQUENCE DESCRIPTION: SEQ ID NO: 2:

GCCGGCCCAG GCTCGGTGAG GAGGCAAGGT TCTGAGGGGA CAGGCTGACC TGGAGGACCA    60

GAGGCCCCCG GAGGAGCACT GAAGGAGAAG ATCTGCCAGT GGGTCTCCAT TGCCCAGCTC   120

CTGCCCACAC TCCCGCCTGT TGCCCTGACC AGAGTCATCA TGCCTCTTGA GCAGAGGAGT   180

CAGCACTGCA AGCCTGAAGA AGGCCTTGAG GCCCGAGGAG AGGCCCTGGG CCTGGTGGGT   240

GCGCAGGCTC CTGCTACTGA GGAGCAGGAG GCTGCCTCCT CCTCTTCTAC TCTAGTTGAA   300

GTCACCCTGG GGGAGGTGCC TGCTGCCGAG TCACCAGATC CTCCCCAGAG TCCTCAGGGA   360

GCCTCCAGCC TCCCCACTAC CATGAACTAC CCTCTCTGGA GCCAATCCTA TGAGGACTCC   420

AGCAACCAAG AAGAGGAGGG GCCAAGCACC TTCCCTGACC TGGAGTCTGA GTTCCAAGCA   480

GCACTCAGTA GGAAGGTGGC CAAGTTGGTT CATTTTCTGC TCCTCAAGTA TCGAGCCAGG   540

GAGCCGGTCA CAAAGGCAGA AATGCTGGGG AGTGTCGTCG GAAATTGGCA GTACTTCTTT   600

CCTGTGATCT TCAGCAAAGC TTCCGATTCC TTGCAGCTGG TCTTTGGCAT CGAGCTGATG   660

GAAGTGGACC CCATCGGCCA CGTGTACATC TTTGCCACCT GCCTGGGCCT CTCCTACGAT   720

GGCCTGCTGG GTGACAATCA GATCATGCCC AAGACAGGCT TCCTGATAAT CATCCTGGCC   780

ATAATCGCAA AGAGGGCGA CTGTGCCCCT GAGGAGAAAA TCTGGGAGGA GCTGAGTGTG   840

TTAGAGGTGT TTGAGGGGAG GGAAGACAGT ATCTTCGGGG ATCCCAAGAA GCTGCTCACC   900

CAATATTTCG TGCAGGAAAA CTACCTGGAG TACCGGCAGG TCCCCGGCAG TGATCCTGCA   960

TGCTATGAGT TCCTGTGGGG TCCAAGGGCC CTCATTGAAA CCAGCTATGT GAAAGTCCTG  1020

CACCATATGG TAAAGATCAG TGGAGGACCT CGCATTTCCT ACCCACTCCT GCATGAGTGG  1080

GCTTTGAGAG AGGGGGAAGA GTGAGTCTGA GCACGAGTTG CAGCCAGGGC CAGTGGGAGG  1140

GGGTTTGGGC CAGTGCACCT TCCGGGGCCC CATCCCTTAG TTTCCACTGC CTCCTGTGAC  1200

GTGAGGCCCA TTCTTCACTC TTTGAAGCGA GCAGTCAGCA TTCTTAGTAG TGGGTTTCTG  1260

TTCTGTTGGA TGACTTTGAG ATTATTCTTT GTTTCCTGTT GGAGTTGTTC AAATGTTCCT  1320

TTTAACGGAT GGTTGAATGA GCGTCAGCAT CCAGGTTTAT GAATGACAGT AGTCA       1375

(2) INFORMATION FOR SEQ ID NO: 3:

(i) SEQUENCE CHARACTERISTICS:
            (A) LENGTH: 21 nucleotides
            (B) TYPE: nucleic acid
            (C) STRANDEDNESS: single
            (D) TOPOLOGY: linear (xi) SEQUENCE DESCRIPTION: SEQ ID NO: 3:

GACCAGAGTC ATCATGCCTC T                                              21

(2) INFORMATION FOR SEQ ID NO: 4:

(i) SEQUENCE CHARACTERISTICS:
            (A) LENGTH: 19 nucleotides
            (B) TYPE: nucleic acid
            (C) STRANDEDNESS: single
            (D) TOPOLOGY: linear (xi) SEQUENCE DESCRIPTION: SEQ ID NO: 4:

TCCTCCACTG ATCTTTACC                                                 19

(2) INFORMATION FOR SEQ ID NO: 5:

(i) SEQUENCE CHARACTERISTICS:
        (A) LENGTH: 12 amino acid residues
        (B) TYPE: amino acid
        (D) TOPOLOGY: linear (xi) SEQUENCE DESCRIPTION: SEQ ID NO: 5:

Lys Ile Ser Gly Gly Pro Arg Ile Ser Tyr Pro Leu
                5                   10

(2) INFORMATION FOR SEQ ID NO: 6:

(i) SEQUENCE CHARACTERISTICS:
        (A) LENGTH: 15 amino acid residues
        (B) TYPE: amino acid
        (D) TOPOLOGY: linear (ix) FEATURE:
        (D) OTHER INFORMATION: Each Xaa may be any amino acid.
            One, two or all of the N-terminus and C-terminus Xaa
            moieties may be absent.

(xi) SEQUENCE DESCRIPTION: SEQ ID NO: 6:

Xaa Xaa Xaa Ile Xaa Xaa Xaa Xaa Arg Xaa Xaa Tyr Xaa Xaa Xaa
                5                   10                  15

(2) INFORMATION FOR SEQ ID NO: 7:

(i) SEQUENCE CHARACTERISTICS:
        (A) LENGTH: 9 amino acids
        (B) TYPE: amino acid
        (D) TOPOLOGY:  linear (ix) FEATURE:
        (D) OTHER INFORMATION: Each Xaa may be any amino acid.

(xi) SEQUENCE DESCRIPTION: SEQ ID NO: 7:

Ile Xaa Gly Xaa Pro Arg Xaa Xaa Tyr
                5

(2) INFORMATION FOR SEQ ID NO: 8:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 8:

Ile Ser Gly Gly Pro Arg Ile Ser Tyr
                5

(2) INFORMATION FOR SEQ ID NO: 9:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO: 9:

Lys Ile Ser Gly Gly Pro Arg Ile Ser Tyr
                5                   10

(2) INFORMATION FOR SEQ ID NO: 10:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 10:

```
Ile Xaa Gly Xaa Xaa Arg Xaa Xaa Tyr
                5

(2) INFORMATION FOR SEQ ID NO: 11:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 11:

Ile Xaa Xaa Xaa Pro Arg Xaa Xaa Tyr
                5

(2) INFORMATION FOR SEQ ID NO: 12:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 12:

Ile Ser Gly Gly Pro His Ile Ser Tyr
```

ISOLATED PEPTIDES WHICH COMPLEX WITH HLA-CW*16 MOLECULES, AND USES THEREOF

This application is a division of application Ser. No. 08/713,354, filed Sep. 13, 1996, pending.

FIELD OF THE INVENTION

This invention relates to immunogenetics and to peptide chemistry. More particularly, it relates to peptides useful in various ways, including immunogens and as ligands for HLA-Cw*16 molecules. More particularly, it relates to so-called "tumor rejection antigens", derived from the tumor rejection antigen precursor encoded by gene MAGE-6, and presented by molecules of MHC class HLA-Cw*16.

BACKGROUND AND PRIOR ART

The study of the recognition or lack of recognition of cancer cells by a host organism has proceeded in many different directions. Understanding of the field presumes some understanding of both basic immunology and oncology.

Early research on mouse tumors revealed that these displayed molecules which led to rejection of tumor cells when transplanted into syngeneic animals. These molecules are "recognized" by T-cells in the recipient animal, and provoke a cytolytic T-cell response with lysis of the transplanted cells. This evidence was first obtained with tumors induced in vitro by chemical carcinogens, such as methylcholanthrene. The antigens expressed by the tumors and which elicited the T-cell response were found to be different for each tumor. See Prehn, et al., J. Natl. Canc. Inst. 18: 769–778 (1957); Klein et al., Cancer Res. 20: 1561–1572 (1960); Gross, Cancer Res. 3: 326–333 (1943), Basombrio, Cancer Res. 30: 2458–2462 (1970) for general teachings on inducing tumors with chemical carcinogens and differences in cell surface antigens. This class of antigens has come to be known as "tumor specific transplantation antigens" or "TSTAs". Following the observation of the presentation of such antigens when induced by chemical carcinogens, similar results were obtained when tumors were induced in vitro via ultraviolet radiation. See Kripke, J. Natl. Canc. Inst. 53: 333–1336 (1974).

While T-cell mediated immune responses were observed for the types of tumor described supra, spontaneous tumors were thought to be generally non-immunogenic. These were therefore believed not to present antigens which provoked a response to the tumor in the tumor carrying subject. See Hewitt, et al., Brit. J. Cancer 33: 241–259 (1976).

The family of tum⁻ antigen presenting cell lines are immunogenic variants obtained by mutagenesis of mouse tumor cells or cell lines, as described by Boon et al., J. Exp. Med. 152: 1184–1193 (1980), the disclosure of which is incorporated by reference. To elaborate, tum⁻ antigens are obtained by mutating tumor cells which do not generate an immune response in syngeneic mice and will form tumors (i.e., "tum⁺" cells). When these tum⁺ cells are mutagenized, they are rejected by syngeneic mice, and fail to form tumors (thus "tum⁻"). See Boon et al., Proc. Natl. Acad. Sci. USA 74: 272 (1977), the disclosure of which is incorporated by reference. Many tumor types have been shown to exhibit this phenomenon. See, e.g., Frost et al., Cancer Res. 43: 125 (1983).

It appears that tum variants fail to form progressive tumors because they initiate an immune rejection process. The evidence in favor of this hypothesis includes the ability of "tum⁻" variants of tumors, i.e., those which do not normally form tumors, to do so in mice with immune systems suppressed by sublethal irradiation, Van Pel et al., Proc. Natl. Acad. Sci. USA 76: 5282–5285 (1979); and the observation that intraperitoneally injected tum⁻ cells of mastocytoma P815 multiply exponentially for 12–15 days, and then are eliminated in only a few days in the midst of an influx of lymphocytes and macrophages (Uyttenhove et al., J. Exp. Med. 152: 1175–1183 (1980)). Further evidence includes the observation that mice acquire an immune memory which permits them to resist subsequent challenge to the same tum⁻ variant, even when immunosuppressive amounts of radiation are administered with the following challenge of cells (Boon et al., Proc. Natl, Acad. Sci. USA 74: 272–275 (1977); Van Pel et al., supra; Uyttenhove et al., supra). Later research found that when spontaneous tumors were subjected to mutagenesis, immunogenic variants were produced which did generate a response. Indeed, these variants were able to elicit an immune protective response against the original tumor. See Van Pel et al., J. Exp. Med. 157: 1992–2001 (1983). Thus, it has been shown that it is possible to elicit presentation of a so-called "tumor rejection antigen" in a tumor which is a target for a syngeneic rejection response. Similar results have been obtained when foreign genes have been transfected into spontaneous tumors. See Fearon et al., Cancer Res. 48: 2975–1980 (1988) in this regard.

A class of antigens has been recognized which are presented on the surface of tumor cells and are recognized by cytolytic T cells, leading to lysis. This class of antigens will be referred to as "tumor rejection antigens" or "TRAs" hereafter. TRAs may or may not elicit antibody responses. The extent to which these antigens have been studied, has been via cytolytic T cell characterization studies, in vitro i.e., the study of the identification of the antigen by a particular cytolytic T cell ("CTL" hereafter) subset. The subset proliferates upon recognition of the presented tumor rejection antigen, and the cells presenting the tumor rejection antigens are lysed. Characterization studies have identified CTL clones which specifically lyse cells expressing the tumor rejection antigens. Examples of this work may be found in Levy et al., Adv. Cancer Res. 24: 1–59 (1977); Boon et al., J. Exp. Med. 152: 1184–1193 (1980); Brunner et al., J. Immunol. 124: 1627–1634 (1980); Maryanski et al., Eur. J. Immunol. 124: 1627–1634 (1980); Maryanski et al., Eur. J. Immunol. 12: 406–412 (1982); Palladino et al., Canc. Res. 47: 5074–5079 (1987). This type of analysis is required for other types of antigens recognized by CTLs, including minor histocompatibility antigens, the male specific H-Y antigens, and the class of antigens referred to as "tum⁻" antigens, and discussed herein.

A tumor exemplary of the subject matter described supra is known as P815. See DePlaen et al., Proc. Natl. Acad. Sci. USA 85: 2274–2278 (1988); Szikora et al., EMBO J 9: 1041–1050 (1990), and Sibille et al., J. Exp. Med. 172: 35–45 (1990), the disclosures of which are incorporated by reference. The P815 tumor is a mastocytoma, induced in a DBA/2 mouse with methylcholanthrene and cultured as both an in vitro tumor and a cell line. The P815 line has generated many tum⁻ variants following mutagenesis, including variants referred to as P91A (DePlaen, supra), 35B (Szikora, supra), and P198 (Sibille, supra). In contrast to tumor rejection antigens—and this is a key distinction—the turf antigens are only present after the tumor cells are mutagenized. Tumor rejection antigens are present on cells of a given tumor without mutagenesis. Hence, with reference to the literature, a cell line can be tum⁺, such as the line referred to as "P1", and can be provoked to produce tum⁻ variants. Since the tum⁻ phenotype differs from that of the parent cell line, one expects a difference in the DNA of tum⁻ cell lines as compared to their tum⁺ parental lines, and this difference can be exploited to locate the gene of interest in tum⁻ cells. As a result, it was found that genes of tum⁻ variants such as P91A, 35B and P198 differ from their normal alleles by point mutations in the coding regions of the gene. See Szikora and Sibille, supra, and Lurquin et al., Cell 58: 293–303 (1989). This has proved not to be the case with the TRAs of this invention. These papers also demonstrated that peptides derived from the tum⁻ antigen are presented by the $L^d$ molecule for recognition by CTLs. P91A is presented by $L^d$, P35 by $D^d$ and P198 by $K^d$.

PCT application PCT/US92/04354, filed on May 22, 1992 assigned to the same assignee as the subject application, teaches a family of human tumor rejection antigen precursor coding genes, referred to as the MAGE family. Several of these genes are also discussed in van der Bruggen et al., Science 254: 1643 (1991). It is now clear that the various genes of the MAGE family are expressed in tumor cells, and can serve as markers for the diagnosis of such tumors, as well as for other purposes discussed therein. See also Traversari et al., Immunogenetics 35: 145 (1992); van der Bruggen et al., Science 254: 1643 (1991) and De Plaen, et al., Immunogenetics 40: 360 (1994). The mechanism by which a protein is processed and presented on a cell surface has now been fairly well documented. A cursory review of the development of the field may be found in Barinaga, "Getting Some 'Backbone': How MHC Binds Peptides", Science 257: 880 (1992); also, see Fremont et al., Science 257: 919 (1992); Matsumura et al., Science 257: 927 (1992); Latron et al., Science 257: 964 (1992). These papers generally point to a requirement that the peptide which binds to an MHC/HLA molecule be nine amino acids long (a "nonapeptide"), and to the importance of the first and ninth residues of the nonapeptide.

Studies on the MAGE family of genes have now revealed that a particular nonapeptide is in fact presented on the surface of some tumor cells, and that the presentation of the nonapeptide requires that the presenting molecule be HLA-A1. Complexes of the MAGE-1 tumor rejection antigen (the "TRA" or "nonapeptide") leads to lysis of the cell presenting it by cytolytic T cells ("CTLs").

Attention is drawn, e.g., to applications Ser. No. 08/217, 188 to Melief et al, Ser. No. 08/217,187 to Traversari et al., and Ser. No. 08/217,186 to Townsend et al., all of which present work on other, MAGE-derived peptides.

Research presented in, e.g., U.S. patent application Ser. No. 07/938,334 filed Aug. 31, 1992, and in U.S. patent application Ser. No. 073,103, filed Jun. 7, 1993, found that when comparing homologous regions of various MAGE genes to the region of the MAGE-1 gene coding for the relevant nonapeptide, there is a great deal of homology. Indeed, these observations lead to one of the aspects of the invention disclosed and claimed therein, which is a family of nonapeptides all of which have the same N-terminal and C-terminal amino acids. These nonapeptides were described as being useful for various purposes which includes their use as immunogens, either alone or coupled to carrier peptides. Nonapeptides are of sufficient size to constitute an antigenic epitope, and the antibodies generated thereto were described as being useful for identifying the nonapeptide, either as it exists alone, or as part of a larger polypeptide.

The human major histocompatibility complex (MHC) system is an involved one. One feature of the system is the human leukocyte antigen, or "HLA". Human cells can be "typed", based upon their HLA profile. Not all cells present all types of HLA molecules. The diversity of this system may be seen by reference to, e.g., Zemmour et al., Immunogenetics 37: 239–250 (1993). This reference shows that, as of 1992, there were literally dozens of different HLA alleles which were known to the art. Cianetti et al., Immunogenetics 29: 80–91 (1989), the disclosure of which is incorporated by reference, discloses, inter alia, an MHC allele referred to therein as HLA-C-clone 10. This allele was later renamed, as per Bodmer et al., Tissue Antigen 44: 1–18 (1994), incorporated by reference. The allele is now known as HLA-Cw*1601. A related allele, i.e., HLA-Cw*1602 is also known. See Bodmer et al, supra; Vilches et al., Human Immunol. 41: 167–170 (1994), also incorporated by reference. These two alleles, when discussed collectively, will be referred to as "HLA-Cw*16". Van der Bruggen et al, Eur. J. Immunol. 24: 2134–2140 (1994), incorporated by reference, teach that cytolytic T cells ("CTLs") recognize a complex of a peptide and an HLA-Cw*1601 molecule. These data are also disclosed in copending U.S. patent application Ser. No. 08/79,110, filed Jun. 17, 1993, now allowed and incorporated by reference, and in U.S. patent application Ser. No. 08/196,630, filed on Feb. 5, 1994, and incorporated by reference. Both applications are assigned to the assignee of the subject application. These two applications disclose that the tumor rejection antigen precursor referred to as "BAGE" is processed to peptides presented by the HLA-Cw*1601 molecule. Specifically, the applications disclose a preferred nonapeptide:

Ala Ala Arg Ala Val Phe Leu Ala Leu (SEQ ID NO: 1), which complexes with HLA-Cw*1601, thereby stimulating the cell line CTL 82/82.

U.S. Pat. No. 5,342,774, incorporated by reference, discloses a family of related nucleic acid molecules which encode tumor rejection antigen precursors referred to as the MAGE tumor rejection antigen precursor. These "TRAPS" are numbered as MAGE-1, MAGE-2, etc. Generally, they are expressed predominantly on tumor cells, normal testes cells being the major exception, and they are processed to peptides presented by various HLA molecules, such as HLA-A1, HLA-A2, and so forth. See, e.g., U.S. Pat. No. 5,405,940, incorporated by reference.

Not all tumor cells express all MAGE TRAPs. Hence, while it is desirable for the field to have information available on specific complexes of peptide and HLA molecules which do stimulate T cells, this is not always easy to secure. One requires a cell which expresses both the required MHC molecule and the required TRAP molecule, and the ability to process the large TRAP molecule to the smaller, tumor rejection antigen or "TRA". Even when a particular peptide binds with an MHC molecule to form a complex, this does not per se guarantee that the complex will stimulate CTL proliferation. In other words while peptide MHC binding is sufficient to identify MHC phenotype on a cell, this binding is necessary but not sufficient to provoke CTL proliferation.

The inventors have found, however, that the TRAP encoded by the MAGE-6 gene is processed to TRAs which bind to MHC Molecules of type HLA-Cw*16, and also provoke proliferation of CTLs thereby. Hence, the invention is directed, inter alia, to these peptides and their various uses, as will be explained in the disclosure which follows.

DETAILED DESCRIPTION OF PREFERRED EMBODIMENTS

EXAMPLE 1

Previous work by, e.g., Van den Eynde et al., Int. J. Cancer 44: 634–640 (1989), incorporated by reference, has shown that human melanoma cells present multiple antigens, recognized by different cytolytic T cell lines ("CILs" hereafter). Four such antigens are referred to by Van den Eynde et al., supra, as MZ2-B, D, E and F. One such CTL is referred to as MZ2-CTL 82/21, and it was used in the experiments which follow.

One well known melanoma cell line is MZ2-MEL, which was derived from an abdominal mestastasis. This cell line was then subjected to limiting dilution to yield subline MZ2-MEL.3.0. The subline, in turn, was cultured for over 150 generations to yield subline MZ2-MEL.3.1. An additional subline, MZ2-MEL.43, was prepared by subjecting MZ2-MEL.3.0 to a mutagen, and then limiting dilution. See Herin et al, Int. J. Cancer 39: 390–396 (1987); Van den Eynde, supra. The three cell lines MZ2-MEL.3.0, MZ2-MEL.3.1, and MZ2-MEL.43 were then used, together with killer cell line K562, in a $^{51}$Cr release assay, following Traversari, et al., Immunogenetics 35: 145–152 (1992), and Boon et al., J. Exp. Med. 152: 1184–1193 (1980), using CTL 82/21, supra.

Figure 1:
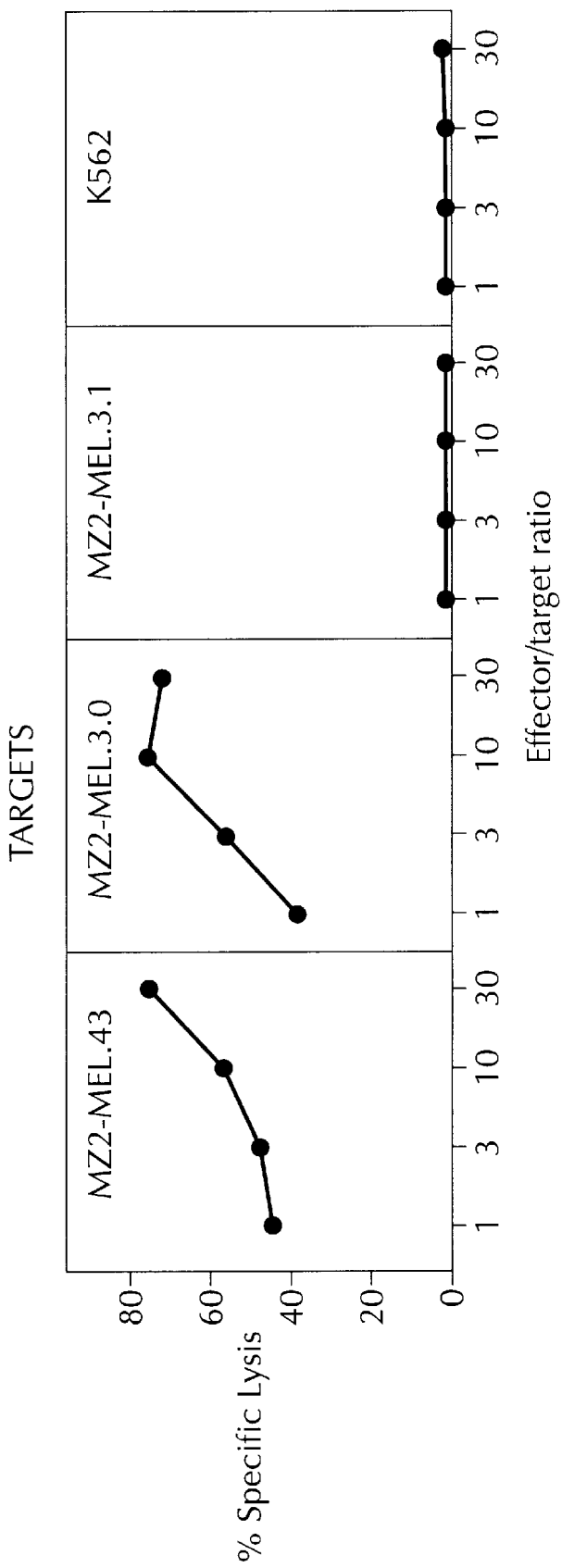
FIG. 1 present data showing that cytolytic T cell line CTL 82/21 lyses lines MZ2-MEL.43 and MZ2-MEL.3.0, but not line MZ2-MEL.3.1, nor does it lyse natural killer cell line K562.

The results, shown in FIG. 1, suggest, inter alia, that MZ2-MEL.3.1 has lost the antigen targeted by CTL 82/21, but that this antigen is found on both MZ2-MEL.3.0 and MZ2-MEL.43. Analysis, in accordance with van der Bruggen et al., Eur. J. Immunol. 24: 2134–2140 (1994), revealed that this cell line had lost the genes encoding HLA-A29, HLA-B44, and HLA-Cw*1601, which differentiated it from both MZ2-MEL.3.0 and MZ2-MEL.3.1. This led to the conclusion that one of these three listed MHC molecules was responsible for the presentation of a peptide which, in combination with the MHC Molecule, led to recognition by CTL 82/21.

EXAMPLE 2

A cDNA sequence encoding HLA-Cw*1601 had been isolated previously, as can be seen in van der Bruggen et al., Eur. J. Immunol. 24: 2134–2140 (1994), incorporated by reference. A cell line which was known to have lost expression of HLA-Cw*1601 was known and available, i.e., MZ2-MEL.2.2.5. This cell line was also known to have lost expression of MAGE-1 (MZ2-MEL.2.2.5 is a subline of MZ2-MEL.2.2, which does express MAGE-1). MZ2 MEL-2.2.5 does express MAGE-2, 3, 6 and 12. As a result, it was a suitable cell line for determining whether or not HLA-Cw*1601, in combination with a peptide, would provoke lysis by cytolytic T cell CTL 82/21.

HLA-Cw*1601 cDNA was inserted into plasmid pcDSRα in accordance with van der Bruggen, et al., Eur. J. Immunol. 24: 2134–2140 (1994). MAGE-1 cDNA was inserted into plasmid pcDNAI via an EcoRI site. Two different plasmids were thus established. The two plasmids were cotransfected into MZ2-MEL2.2.5, together with a plasmid which imparts resistance to G418 (i.e., pSVtkneo8), in accordance with the calcium phosphate method of van der Bruggen et al., Science 254: 1634 (1991).

Transfectants were first selected for resistance to G418, and then tested for expression of MAGE-1 and HLA-Cw*1601 using CTL 81/21, by determining whether or not they could stimulate TNF production in accordance with Traversari et al., Immunogenetics 35: 145–152 (1992). In brief, 1500 CTLs were added to 100 ul Iscove's medium supplemented with 10% human serum and 25 U/ml recombinant human IL-2. This mixture was combined with transfected MZ-MEL.2.2.5 cells, cultured for 24 hours, and then the supernatant was collected. The TNF content was determined by testing the cytotoxicity on WEHI-164 clone 13 cells, in accordance with Espevik et al., J. Immunol. Meth. 95: 99–105 (1986), in an MTT calorimetric assay as described by Hansen et al., J. Immunol. Meth. 119: 203–21 (1989); Traversari et al., Immunogenetics 35: 145–152 (1992).

Figure 2:
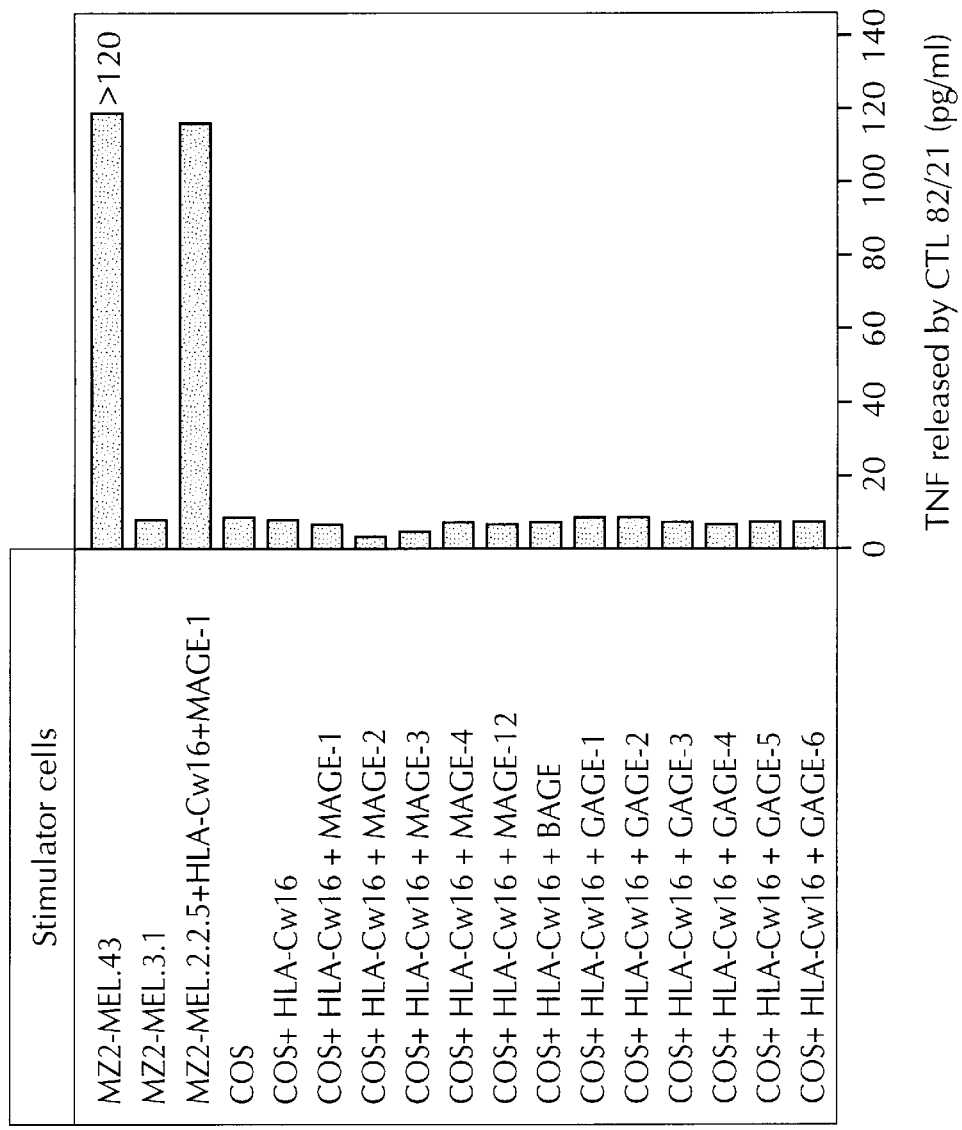
FIG. 2 sets forth results of assays to determine if various cell lines, transfected, cotransfected, and nontransfected, stimulate TNF release by CTL 82/21.

The first three bars of FIG. 2 show these results, using cell lines MZ2-MEL.43 and MZ2-MEL.3.1 as controls. The transfection of MZ2-2.2.5 clearly resulted in stimulation of CTL 82/21. What was not clear from this work, however, was whether or not MAGE-1 was necessary for the stimulation.

EXAMPLE 3

To clarify the issue raised following the experiments in example 2, COS-7 cells were transfected by the DEAE-Dextran chloroquine method of Brichard et al., J. Exp. Med. 178: 489–495 (1993); Coulie, et al., J. Exp. Med. 180: 35–42 (1994); Seed et al., Proc. Natl. Acad. Sci. USA 84: 3365–3369 (1987), and tested in the same manner the MZ2-MEL.2.2.5 cells were tested. In addition to MAGE-1, other TRAP encoding cDNAs were used, including MAGE-2, 3, 4 and 12, BAGE, Melan-A, tyrosinase, and GAGE-1, 2, 3, 4, 5 and 6. As FIG. 2 shows, none of these transfectants led to stimulation of CTL 82/21. As was noted, supra, MZ2-MEL.2.2.5 expresses MAGE-2, 3, 6 and 12 naturally, and was transfected to express MAGE-1. One of the differences between the two sets of experiments is the presence of MAGE-6 in the MZ2-MEL.2.2.5 cell line.

EXAMPLE 4

As a follow up to the experiments of example 3, a cDNA library was prepared from MZ2-MEL.43, and inserted into pCDSRa, using standard methods. The library was transfected into COS cells, together with a plasmid containing HLA-Cw*1601 in pcDSRα, using the methodologies of example 2, supra, and were then tested for TNF release, also as described, supra. Two positive clones were obtained. The plasmid DNA for the positive clones were electroporated into bacteria (E. coli DH5α), using well known methods.

Following the identification of positive colonies, the plasmid DNA was extracted, and about ⅓ was transfected into COS-7 cells together with the HLA-Cw*1601 construct. Clone GEP 3/317 2/B7 conferred recognition by CTL 82/21. Upon sequencing, the clone was identified as MAGE-6, as described by DePlaen et al., Immunogenetics 40: 360–369 (1994), incorporated by reference. SEQ ID NO: 2 sets this sequence forth.

EXAMPLE 5

As MAGE-6 was identified as the TRAP which was processed to the presented peptide, studies were carried out to determine the particular peptide of relevance.

To do this, PCR primers:

GACCAGAGTC ATCATGCCTC T    (SEQ ID NO: 3)

and

TCCTCCACTG ATCTTTACC       (SEQ ID NO: 4)

were used. These were sense and antisense primers, respectively, corresponding to nucleotides 147–167 and 1029–1047 of cDNA for MAGE-6 of SEQ ID NO: 2.

PCR amplification was carried out on clone GEP 3/317 2/B7. After four minutes at 94° C., PCR was carried out for 20 cycles (1 cycle: 1 minute at 94° C., 2 minutes at 60° C., and 2 minutes at 72° C.), followed by 15 minutes at 72° C. PCR product was then inserted into plasmid pCR3, using standard methods, and transfected into COS-7. The resulting transfectant did not code for the antigen.

When the truncated form was compared to the "base clone", i.e., GEP 3/317 2B/7, via sequence analysis, it was noted that the PCR product consisted of nucleotides 147 to 1047 of the ORF, while the base clone consisted of nucleotides 160–1104, indicating that the antigenic peptide necessarily had a C-terminus in nucleotides 1047–1104.

Based upon this hypothesis, a series of peptides were constructed, and lyophilized prior to testing. The lyophilized peptides were dissolved in 1 volume of DMSO, then 9 volumes of $H_2O$, plus 10 mM of acetic acid. The thus diluted peptides were stored at −20° C.

The ability of the peptides to stimulate lysis by CTLs was tested via the $^{51}$Cr release method of Boon et al., J. Exp. Med. 152: 1184–1193 (1980). Specifically, an HLA-Cw*1601 positive lymphoblastoid cell line, i.e., LB678-EBV was $^{51}$Cr labelled for one hour at 37° C., and washed extensively. Then 1000 of these target cells were incubated in 96 well microplates, in the presence of various concentrations of peptide, for 15 minutes, at room temperature. CTLs were then added, and $^{51}$Cr release was measured after four hours, at 37° C.

Figure 3:
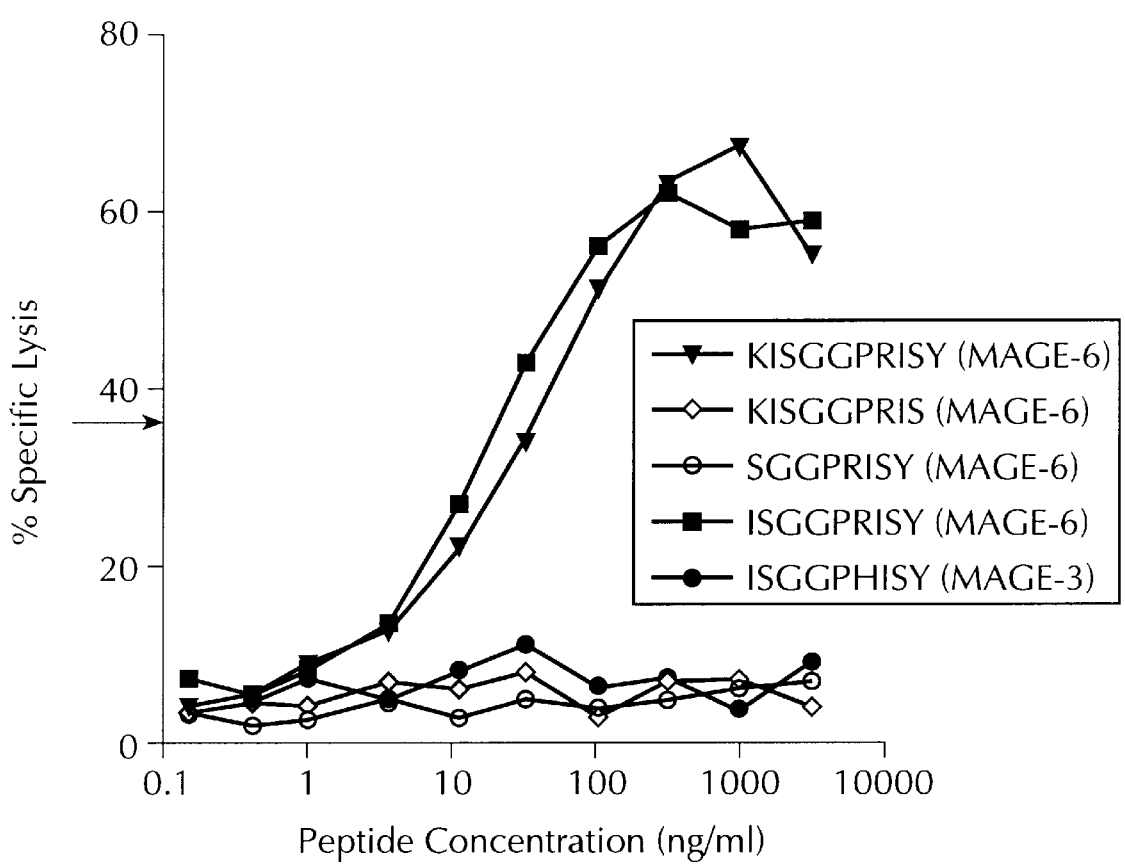
FIG. 3 shows the result of lysis studies, using peptides derived from SEQ ID NO: 2 KISGGPRISY (SEQ. ID. NO. 9), KISGGPRIS (amino acid residues 1–9 of SEQ. ID. NO. 9), SGGPRISY (amino acid residues 3–10 of SEQ. ID. NO. 9), ISGGPRISY (amino acid residues 2–10 of SEQ. ID. NO. 9), ISGGPHISY (SEQ. ID. NO. 12)

Lysis first occurred with the peptide:

Lys Ile Ser Gly Gly Pro Arg Ile Ser Tyr Pro Leu (SEQ ID NO: 5), which corresponds to amino acids 126–137 of MAGE-6. Shorter peptides were also tested, and it was found that the nonamer consisting of amino acids 2–10 of SEQ ID NO: 5 achieved half maximal lysis at a peptide concentration of 30 nM. This is seen in FIG. 3.

The nonapeptide corresponds to a sequence found in MAGE-3, with one exception, i.e., the Arg of the nonapeptide is His in MAGE-3. A nonapeptide corresponding to the MAGE-3 sequence was synthesized, and tested, but was found not to stimulate lysis. Similarly, when peptides were tested which consisted of amino acids 1–9 of SEQ ID NO: 5, and amino acids 3–10 of SEQ ID NO: 5, it was found that neither one stimulated lysis.

Thus, peptides which bind to HLA-Cw*1601 which bind to HLA-Cw*1601 may be defined as peptides where Ile is N-terminal to Tyr, and these two residues are separated by seven amino acids. The fifth of these separating amino acids must be Arg, and Ile does not have to be the N-terminus of the peptide, nor does Tyr have to be the C-terminus because, as noted supra, the peptide of SEQ ID NO: 5 does bind to HLA-Cw*1601 and provokes lysis by cytolytic T cells.

Hence, one aspect of the invention are isolated peptides of formula:

$NH_2$-Xaa-Ile-Xaa-Xaa-Xaa-Xaa-Arg-Xaa-Xaa-Tyr-Xaa-COOH (SEQ ID NO: 6), wherein N terminal Xaa and C-terminal Xaa are anywhere from 0 to 3 amino acids in total, and can be any amino acid. Especially preferred are molecules such as SEQ ID NO: 5, wherein N-terminal Xaa is one amino acid, and C-terminal Xaa is two amino acids. Also preferred are molecules where $NH_2$-Xaa and Xaa-COOH are not present, such as the peptide defined by amino acids 2–10 of SEQ ID NO: 5. These peptides are peptides which bind to MHC molecules of the HLA-Cw*16 type, e.g., HLA-Cw*1601 and HLA-Cw*1602, and preferably provoke lysis by CTLs specific therefor. Thus, one can identify HLA-Cw*16 presenting cells via use of these peptides, including peptides labelled with a detectable signal. The peptides can also be used to provoke lysis of HLA-Cw*1601 presenting cells, if the peptides are present in amounts sufficient to complex HLA-Cw*16 molecules on cellular surfaces. This can be done via, e.g., contacting the cells with the peptides, or transforming or transfecting host cells with one of both of nucleic acid molecules encoding HLA-Cw*16, and MAGE-6. Either or both of these may be gDNA or cDNA.

Some work has been done on binding motifs for HLA-C molecules, although it is by no means as developed as that which has been carried out for HLA-A molecules. See, e.g., Falk et al., Proc. Natl. Acad. Sci. USA 90: 12005–12009 (1993), and Ramensee et al., Immunogenetics 41: 178–228 (1995), both of which are incorporated by reference. These references, Falk in particular, suggest that in the case of nonamers which bind to HLA-C molecules, positions 3, 5 and 6 are important. Hence, with reference to SEQ ID NO: 6, especially preferred are molecules where $NH_2$-Xaa and Xaa-COOH are absent, wherein the following formula results:

Ile Xaa Xaa Xaa Xaa Arg Xaa Xaa Tyr wherein the third amino acid is Gly, and/or the fourth amino acid is Pro (SEQ ID NO. 7,10 or 11). Especially preferred are nonapeptides where the third Xaa in is Gly and the fifth amino acid is Pro. All other residues may be any other amino acid.

In connection with this aspect of the invention, it was noted that nucleotides 1047 through 1104 of MAGE-6 cDNA, as set forth in SEQ ID NO: 2, encode at least the C-terminus of the pertinent tumor rejection antigen. The location of the antigenic peptide of SEQ ID NO: 5 was determined to start at nucleotide 1033 of SEQ ID NO: 2. Hence, a further aspect of this invention is the isolated nucleic acid molecule consisting of nucleotides 1033 through 1104 of SEQ ID NO: 2. This sequence is useful alone, e.g., as a probe for determining expression of MAGE-6, or it can be used in an expression vector, operably linked to a promoter, to express the relevant tumor rejection antigen. Cells which have been transformed or transfected with this nucleic acid molecule, alone or in combination with nucleic acid molecules encoding an HLA-Cw*16 encoding nucleic acid molecule are also a feature of this invention.

The identification of the TRA and the identification of its complexing MHC molecule makes it possible to develop a therapeutic method for treating subjects with disorders characterized by expression of HLA-Cw*16 molecules, such as SEQ ID NO: 5 when presented as the TRA, or as complexes of TRA and HLA, such as HLA-Cw*16, may be combined with materials such as adjuvants to produce vaccines useful in treating disorders characterized by expression of the TRAP molecule. In addition, vaccines can be prepared from cells which present the TRA/HLA complexes on their surface, such as non-proliferative cancer cells, non-proliferative transfectants, etcetera. In all cases where cells are used as a vaccine, these can be cells transfected with coding sequences for one or both of the components necessary to prove a CTL response, or be cells which express both molecules without transfection. Further, the MAGE-6 molecules, its associated TRAs, such as those disclosed herein as well as complexes of TRA and HLA, may be used to produce antibodies, using standard techniques well known to the art.

When "disorder" is used herein, it refers to any pathological condition where the tumor rejection antigen precursor is expressed. An example of such a disorder is cancer, melanoma in particular.

Therapeutic approaches based upon the disclosure are premised on a response by a subject's immune system, leading to lysis of TRA presenting cells, such as HLA-Cw*16 presenting cells. One such approach is the administration of CTLs specific to the complex to a subject with abnormal cells of the phenotype at issue. It is within the skill of the artisan to develop such CTLs in vitro. Specifically, a sample of cells, such as blood cells, are contacted to a cell presenting the complex and capable of provoking a specific CTL to proliferate. The target cell can be a transfectant, such as a COS cell of the type described supra. These transfectants present the desired complex on their surface and, when combined with a CTL of interest, stimulate its proliferation. COS cells, such as those used herein are widely available, as are other suitable host cells.

To detail the therapeutic methodology, referred to as adoptive transfer (Greenberg, J. Immunol. 136(5): 1917 (1986); Reddel et al., Science 257: 238 (Jul. 10, 1992); Lynch et al., Eur. J. Immunol. 21: 1403–1410 (1991); Kast et al., Cell 59: 603–614 (Nov. 17, 1989)), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the relevant HLA/TRA complex. This can be determined very easily, as the art is very familiar with methods for identifying cells which present a particular HLA molecule, as well as how to identify cells expressing DNA of the pertinent sequences, in this case the MAGE-6 sequence. Once cells presenting the relevant complex are identified via the foregoing screening methodology, they can be combined with a sample from a patient, where the sample contains CTLs. If the complex presenting cells are lysed by the mixed CTL sample, then it can be assumed that a BAGE derived, tumor rejection antigen is being presented, and the subject is an appropriate candidate for the therapeutic approaches set forth supra.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated melanoma cells or cells transfected with one or both of the genes necessary for presentation of the complex. Chen et al., Proc. Natl. Acad. Sci. USA 88: 110–114 (January, 1991) exemplifies this approach, showing the use of transfected cells expressing HPVE7 peptides in a therapeutic regime. Various cell types may be used. Similarly, vectors carrying one or both of the genes of interest may be used. Viral or bacterial vectors are especially preferred. In these systems, the gene of interest is carried by, e.g., a Vaccinia virus or the bacteria BCG, and the materials de facto "infect" host cells. The cells which result present the complex of interest, and are recognized by autologous CTLS, which then proliferate. A similar effect can be achieved by combining the tumor rejection antigen or the precursor itself with an adjuvant to facilitate incorporation into HLA-Cw*16 presenting cells which present the HLA molecule of interest. The TRAP is processed to yield the peptide partner of the HLA molecule while the TRA is presented without the need for further processing.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Isolated nucleic acid molecule consisting of nucleotides 1033 through 1104 of SEQ ID NO: 2.

2. Expression vector comprising the isolated nucleic acid molecule of claim 1, operably linked to a promoter.

3. Cell line or cell strain, transformed or transfected with the expression vector of claim 2.

* * * * *